(12) United States Patent
Ryu et al.

(10) Patent No.: US 11,096,731 B2
(45) Date of Patent: Aug. 24, 2021

(54) ORTHOPAEDIC FRACTURE REDUCTION-FIXATION TOOL

(71) Applicants: Jaiyoung Ryu, Morgantown, WV (US); Terry L. Whipple, Richmond, VA (US)

(72) Inventors: Jaiyoung Ryu, Morgantown, WV (US); Terry L. Whipple, Richmond, VA (US)

(*) Notice: Subject to any disclaimer, the term of this patent is extended or adjusted under 35 U.S.C. 154(b) by 203 days.

(21) Appl. No.: 16/150,569

(22) Filed: Oct. 3, 2018

(65) Prior Publication Data

US 2019/0105090 A1 Apr. 11, 2019

Related U.S. Application Data

(60) Provisional application No. 62/569,796, filed on Oct. 9, 2017.

(51) Int. Cl.
| | |
|---|---|
| *A61B 17/86* | (2006.01) |
| *A61B 17/17* | (2006.01) |
| *A61B 17/88* | (2006.01) |
| *A61B 17/16* | (2006.01) |
| *A61B 17/68* | (2006.01) |
| *A61B 17/02* | (2006.01) |

(52) U.S. Cl.
CPC ........ *A61B 17/864* (2013.01); *A61B 17/1782* (2016.11); *A61B 17/8866* (2013.01); *A61B 17/025* (2013.01); *A61B 17/1615* (2013.01); *A61B 17/1637* (2013.01); *A61B 2017/681* (2013.01)

(58) Field of Classification Search
CPC .. A61B 17/864; A61B 17/1615; A61B 17/025

USPC ............................... 600/201–245; 606/96–98
See application file for complete search history.

(56) References Cited

U.S. PATENT DOCUMENTS

| | | | | |
|---|---|---|---|---|
| 5,250,055 | A * | 10/1993 | Moore ............... | A61B 17/1796 606/148 |
| 2002/0032447 | A1* | 3/2002 | Weikel ............... | A61B 17/7061 606/86 R |
| 2008/0269743 | A1* | 10/2008 | McNamara ......... | A61B 17/1615 606/60 |
| 2009/0048575 | A1* | 2/2009 | Waters ............... | A61B 17/1735 604/506 |
| 2009/0222013 | A1* | 9/2009 | Graf ................... | A61B 17/1764 606/87 |
| 2016/0074049 | A1* | 3/2016 | Russell .............. | A61B 17/1721 606/96 |

\* cited by examiner

*Primary Examiner* — Eduardo C Robert
*Assistant Examiner* — Tara Rose E Carter
(74) *Attorney, Agent, or Firm* — John H. Thomas, P.C.

(57) ABSTRACT

A reduction and fixation tool has two principle component parts—an intra-articular spoon with a blade, and a handle that docks with the spoon. The spoon has a proximal hub onto which the handle docks. In one example of the tool as it would be used with a fractured scaphoid, the spoon has a distal blade, curved and narrow to slip beneath the undersurface of the scaphoid and to lift the distal fragment of the bone back into proper alignment (fracture reduction). The handle, docked to the spoon, serves as a lever to easily accomplish the reduction, and as a guide for the central insertion of a guide wire into the scaphoid across the fracture site.

9 Claims, 17 Drawing Sheets

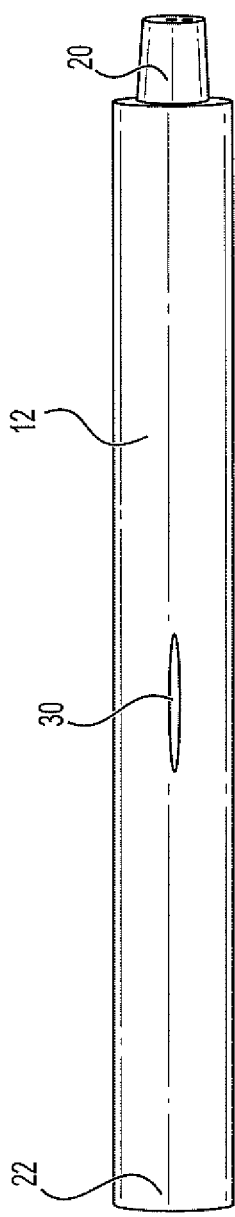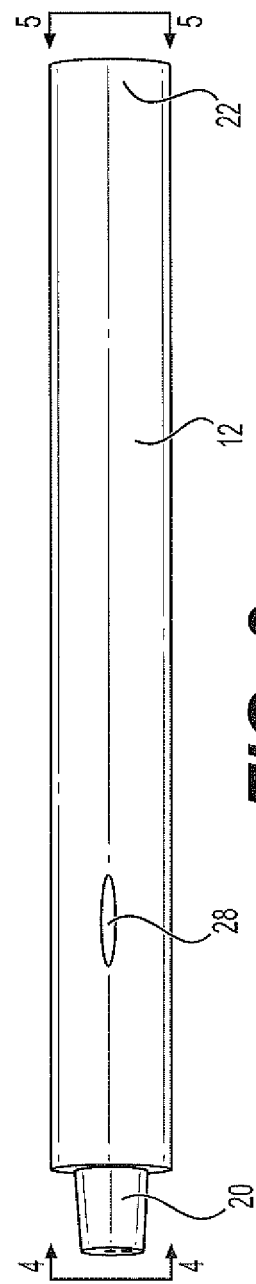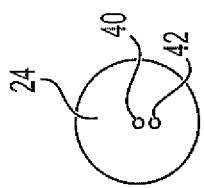

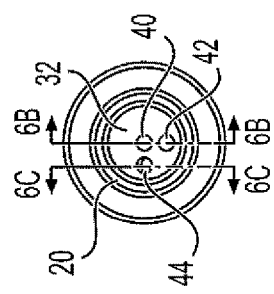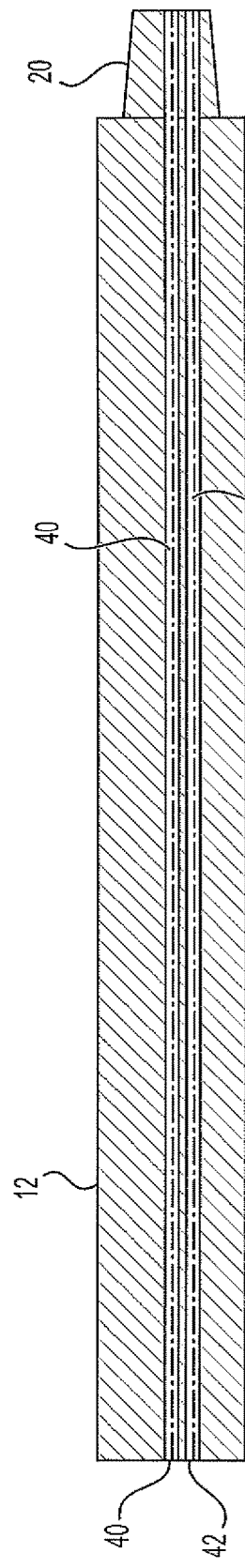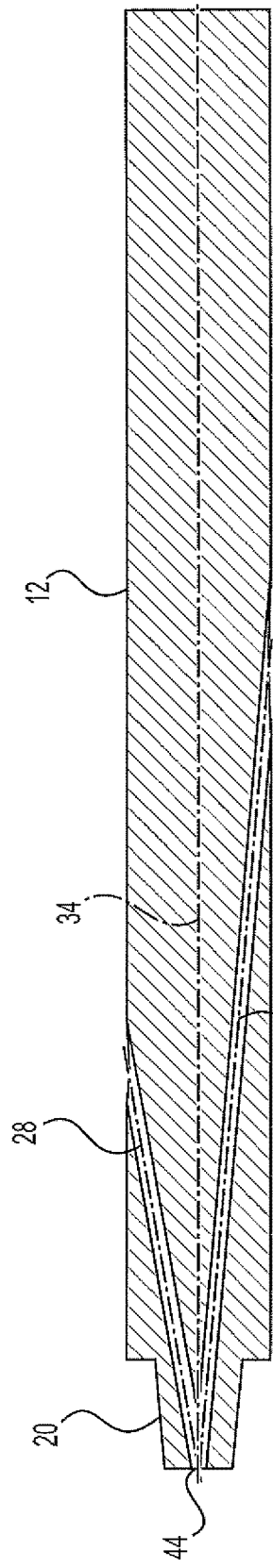

ORTHOPAEDIC FRACTURE REDUCTION-FIXATION TOOL

This application claims the benefit of U.S. Provisional Patent Application No. 62/569,796, filed Oct. 9, 2017, which is incorporated by reference herein in its entirety.

The reduction and fixation tool described herein includes a spoon and a handle component that aids in the relatively, minimally intrusive reduction of a bone fracture. The structure of the handle then aids in the fixation of the fractured bone in reasonable alignment. In one example, the reduction and fixation tool and related method are useful in aligning and fixing a broken scaphoid bone.

BACKGROUND

The scaphoid is the most commonly fractured carpal bone in the wrist. The U.S. National Electronic Injury Surveillance System (NEISS) has estimated an incidence of 4,500 scaphoid fractures per year. An article in the British Journal of Bone and Joint Surgery estimated 37,200 fractures per year in the U.K. Whichever is more accurate, the number is large. Some 80% of scaphoid fractures involve the narrow waist of the bone.

Treatment options for scaphoid fractures include fracture reduction, casting, pinning or surgical exposure and fixation of the fracture. The worldwide trend for preferred treatment is for early surgical fixation with minimally invasive techniques. Concerns and cautions include adequate fracture reduction, rigid stabilization, protection of soft tissue ligaments, protection of a tenuous blood supply to and inside the scaphoid bone, earlier return to functional independence and the ultimate functional and cosmetic results. Clearly, this is a problematic and challenging fracture.

Surgical exposure for adequate fracture reduction can require relatively large surgical incisions that jeopardize the ligaments and blood circulation to the scaphoid. Firm stabilization of the fracture fragments utilizes a central screw placed preferably from proximal to distal to avoid disruption of the blood supply. Cannulated screws have been designed for placement over a central guide wire, but accurate placement of the guide wire is extremely difficult. Multiple placement attempts can disrupt the precious articular cartilage on the proximal pole of the scaphoid, leading eventually to wrist arthritis. Other fractures occur that are similarly difficult to treat surgically with internal fixation.

SUMMARY

The fracture reduction and fixation tool described herein incorporates features designed to facilitate more convenient and more accurate reduction and stabilization of many such fractures, utilizing minimally invasive surgical techniques and protecting the soft tissue structures around the broken bone. The reduction and fixation tool has two principle component parts—an intra-articular spoon with a blade, and a handle that docks with the spoon. The spoon has a proximal hub onto which the handle docks. In one example of the tool, as it would be used with a fractured scaphoid bone in the wrist, the spoon has a distal blade, curved and narrow to slip beneath the undersurface of the scaphoid and to lift the distal fragment of the bone back into proper alignment (fracture reduction). Through a small incision on the back of the wrist, in line with normal skin creases for cosmetic results, the spoon blade is inserted to accomplish fracture reduction. The leading tip of the spoon blade fits readily into the tight, narrow joint capsule space surrounding the distal portion of the scaphoid that is displaced by the fracture. The handle, docked to the spoon, serves as a lever to easily accomplish the fracture fragment reduction and as an instrument for the central insertion of a guide wire into the scaphoid across the fracture site. X-ray confirms the central placement of the guide wire, which can be readily adjusted if necessary utilizing alternate channels within the same handle, and a cannulated screw can be placed over the guide wire into the bone, stabilizing the fracture.

In one example, a reduction and fixation tool for use in orthopaedic fracture repair comprises a spoon and a handle, wherein the spoon is comprised of a proximal hub and a distal blade, wherein the distal blade is substantially flat but has a contoured portion of a distal edge of the blade. The handle has a length and has a first end and second end on opposite ends of the handle, wherein the handle has a first face on the first end and second face on the second end of the handle, and wherein the first end of the handle is positioned inside the proximal hub of the spoon. The hub has a linear aperture therethrough that is open on a forward side above the blade portion of the spoon, and the handle is cannulated and has a bore therethrough that is open at the first face of the handle. The bore may have a longitudinal orientation through the entire length of the handle and that is open at both the first face and second face of the handle. The bore may be generally positioned through the longitudinal center of the handle and is open at substantially the center of the first face. The handle may comprise a plurality of bores therethrough, and the plurality of bores are all open at a same position on the first face of the handle. Alternatively, the handle may comprise a plurality of bores therethrough, and the plurality of bores are open at a plurality of different positions on the first face of the handle. In this alternative, each bore may have its own, different open position on the first face of the handle, or each of the plurality of bores may be parallel to each other. The hub aperture may be round and defines an inside diameter, wherein the handle first end is round in cross section and defines an outside diameter, and wherein the inside diameter of the hub aperture is slightly larger than the outside diameter of the first end of the handle to enable circular rotation of the handle in the hub. The contoured portion of the distal edge of the blade may be a shape selected from the group consisting of a point, a barb, a fork, and a cup.

In another example, a method of reduction and fixation of a scaphoid bone fracture comprises multiple steps. The steps include providing a reduction and fixation tool comprising a spoon and a handle, wherein the spoon is comprised of a proximal hub and a distal blade, wherein the distal blade is substantially flat but has a contoured portion of a distal edge of the blade. The handle has a length and has a first end and second end on opposite ends of the handle, wherein the handle has a first face on the first end and second face on the second end of the handle, and wherein the first end of the handle is positioned inside the proximal hub of the spoon. The hub has a linear aperture therethrough that is open on a forward side above the blade portion of the spoon. The handle is cannulated and has a bore therethrough that is open at the first face of the handle. The method also includes making an incision on the back of the wrist of a patient; positioning the spoon under the scaphoid bone of the patient; lifting a distal fragment of the patient's scaphoid bone into a desired anatomical alignment. The handle bore is positioned adjacent the scaphoid bone and a guide wire is inserted through the bore and into the scaphoid bone and across the fracture. The handle is disengaged from the hub of the spoon and removed. The bone is reamed with a cannulated reamer over the guide wire to make a track for placement of a screw, and then a cannulated screw is placed over the guide wire and screwed into the scaphoid bone and across the fracture site and into the distal bone fragment to stabilize the fracture for healing. The method may further comprise the step of taking a fluoroscopic or radiographic scan of the scaphoid bone after the guide wire is inserted and before the screw is fixed into the bone in order to confirm the correct, central placement of the guide wire in the bone.

BRIEF DESCRIPTION OF THE DRAWINGS

FIG. 2 is a perspective view of a handle for a fracture reduction and fixation tool as described herein also showing the front face of the handle.

FIG. 3 is a perspective view of the opposite side of a handle for a fracture reduction and fixation tool as shown in FIG. 2 and as described herein also showing the front face of the handle.

FIG. 4 is a front view of a handle showing three apertures on the front face thereof.

FIG. 5 is a back view of a handle showing two apertures on the back face thereof.

FIG. 6A shows a front view of a handle with three apertures in the face thereof. FIG. 6B shows a side cross-sectional view of the handle in FIG. 6A taken along lines 6B-6B. FIG. 6C is a side, cross-sectional view of the handle in FIG. 6A taken along lines 6C-6C.

DETAILED DESCRIPTION

Figure 1:
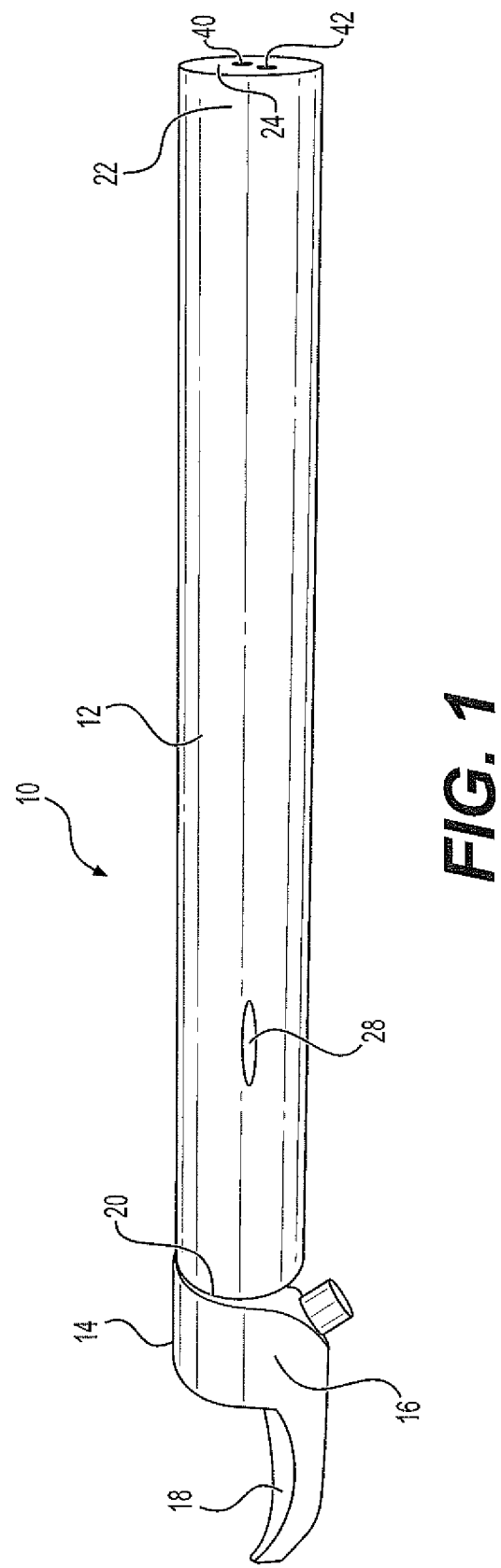
FIG. 1 is a perspective view of one example of a fracture reduction and fixation tool as described herein.

Much of the discussion and drawings contained herein are directed to an example of a tool used as a reduction and fixation tool in scaphoid bone fracture procedures. However, generally speaking, those of skill in the art will be able to use the same spoon and handle combination tool in addressing other bone fractures. Examples of these other fracture fixation capabilities include clavicle, humerus greater tuberosity, olecranon, radius styloid, hamate, first metacarpal, patella, tibia plateau, posterior or medial tibia malleolus, fibula lateral malleolus, calcaneus, fifth metatarsal, ischial or pubic ramus, mandible. The shape and dimensions of a handle would be the same or similar to the handle examples herein. A bore in the handle may have a different sized diameter (cross section) than disclosed channels depending on the guide wires used with a specific fracture. Also the shape of the first end of the handle may be cylindrical, as opposed to truncated in the scaphoid example described and illustrated. Simple alterations of the spoon blade tips and sizes (lengths, widths and contours) facilitate adaptation to specific bone shapes. The spoon tip may be modified with a hook or barb or other shape to facilitate control of the distal fracture fragment to be manipulated into reduction with the more proximal fragment. The same concept is then employed to introduce a guide wire across the fracture site, entering the proximal fragment from its appropriate side or end to advance a pin or screw into the distal bone fragment. Distal fracture fragments of bones can be reduced and stabilized when the tool is introduced from a more proximal, minimally-invasive incision to avoid extensive soft tissue dissection.

The spoon and handle portions of the tool are discussed separately first and then in an interactional way. The handle is a longitudinal piece with a first end and a second end. Typically, the handle is formed of medical grade stainless steel or some similar metallic hybrid mixture or a rigid, radiolucent synthetic material. It may or may not be designed for reuse with traditional autoclave and cleaning between uses. The first end of the handle, referred to herein as the front end, is engineered to dock with the spoon. The handle is removable from the spoon for the purposes of use in a surgical procedure when the handle is used for some steps but removed for others.

The handle has one or more bores therethrough. The bore can be parallel with or right along the central axis of a handle cross-section. For instance, if the handle has a round cross-section, then the bore can be substantially in the center of the circle. Alternatively, the bore may be offset from the central axis. Still further, the bore may be angled as compared with the central axis of the handle. There is an opening of the bore on the front face of the first end of the handle. Depending on the angle or slope of the bore through the handle, there will be an opening of the bore on the back face of the second end of the handle. The cross-sectional diameter of this bore, typically a round bore, will be sized to allow a guide wire to pass through the bore and to rotate within the bore. The range of a bore opening, in the example of a round opening and round cross-section bore, is from about 0.025 to 0.1 inches, or alternatively about 0.05 to 0.075 inches.

In addition to the example of a single bore through the handle, there may be a plurality of bores that are formed through the handle. One or more additional bores may be parallel to a central bore. Additional bores may be offset at different distances from the central bore of the handle. While each bore will be open to the front face of the first end of the handle, there may also be angled bores that are open on their opposite end on the side of the handle. For instance, there can be a 5 degree angle bore, a 10 degree angle bore, or other combinations of angled bores. Each different bore of the plurality of bores can have its own opening on the front face of the handle. Alternatively, two or more different bores may have the same opening on the front face of the handle. Therefore, a handle may have both parallel bores and angled bores and different or one or more common openings. The number and orientation of the bore or bores through a handle may be engineered for the preference of a surgeon or for the expected best positioning for a given surgery.

The spoon portion of the tool has a blade and a hub. The hub is engineered to releasably engage and secure the handle to the spoon. The hub includes an aperture positioned so that the front face of the hub is open and accessible to the space above the top of the blade. In use, the front face of the handle will be proximate to the bone with the blade portion of the spoon being under the bone. The hub can have a round aperture to receive the first end of the handle, or alternatively, the aperture may be a different symmetric or asymmetric shape to receive the handle. The hub may define a complete circle (or other aperture) all around a handle, or the hub may extend only partly around the first end of the handle.

In one example, the hub aperture is round, and the first end of the handle is round and substantially mates with the aperture. Importantly, the handle may rotate around in the circle. In this way, the bore(s) in the handle may rotate so that a guide wire may be directed into a different location or at a different angle in a fractured bone at the discretion of a surgeon.

The blade is preferably relatively thin, so that it does not disturb the surrounding ligaments or vasculature of a fractured bone, yet the blade must be rigid and stout enough to leverage a bone fragment into a position of alignment. Alternatively, for different shaped bones and fractures, the rigid blade may be of different lengths, widths and contours to accommodate the particular shape of the involved bone and the soft tissue structures surrounding the bone at the fracture site. The contoured portion of the distal edge of the blade can be a shape selected from the group consisting of a point, a barb, a fork, and a cup. For various bone fractures, the blade may be passed either across a joint space (as with the herein described scaphoid fracture) or through soft tissue planes to reach the displaced bone fracture fragment for manipulation.

The tool is typically formed of metal, such as stainless steel or other durable metal. Alternatively, it may be constructed of a rigid, radiolucent material which would facilitate intra-operative imaging of the fracture fragments and guide wire placement.

Turning now to the figures, there is shown a tool 10 in various views in FIGS. 1-9. In FIG. 1, the tool 10 is formed of a handle 12 and a spoon 14. The handle 12 has a first end 20 and a second end 22. A back face 24 is on the second end 22. The tool 10 has a spoon 14 that is made up of a hub 16 and a blade 18. The handle 12 has a side bore 28 open on the side of the handle. A center bore 40 and offset bore 42 are shown on the back face 24 on the second end 22 of the handle.

FIG. 2 is a view of the handle 12 only. This view of the handle 12 in FIG. 2 is taken from the opposite side as FIG. 1. In this view there is another angled bore 30 that is open on this opposite side of the handle 12. The first end 20 is shown as a frusto-conical shape. In FIG. 4, the face 32 of the first end 20 has three holes that are the openings of three bores 40, 42 and 44. The back face 24 in FIG. 5 shows the openings of the two longitudinal bores 40 and 42.

FIG. 6A is a similar front view of the first end 20 and specifically the front face 32. This FIG. 6A shows the cross-sectional views taken in FIGS. 6B and 6C. In FIG. 6B, there are two parallel bores 40 and 42 that run the length of the handle 12. Bore 40 runs along the central axis of the handle 12, while bore 42 is offset to one side of the handle but parallel to the central bore. In FIG. 6C, there are shown two differently angled bores 28 and 30. Each of these bores 28 and 30 is open on the front face 32 at opening 44. Bore 28 is 10 degrees from the central axis 34, while bore 30 is 5 degrees from the central axis.

Figure 7:
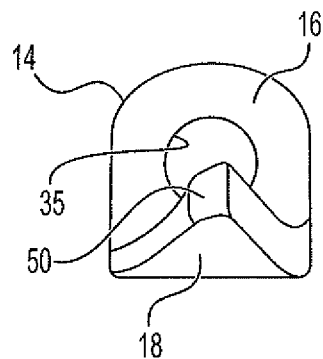
FIG. 7 is a front view of one example of a spoon component of a fracture reduction and fixation tool as described herein.
Figure 8:
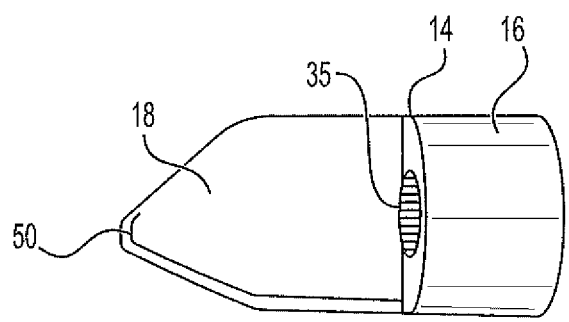
FIG. 8 is a top view of the spoon shown in FIG. 7.
Figure 9:
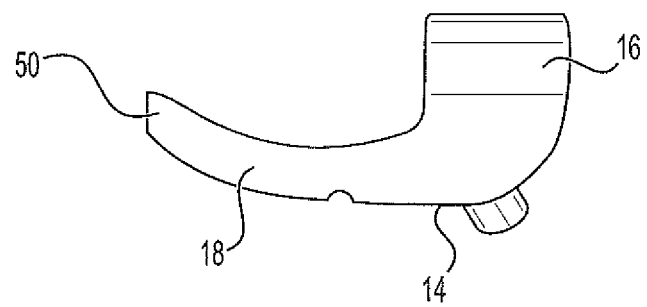
FIG. 9 is a left side view of the spoon shown in FIG. 7.

FIGS. 7-9 illustrate the spoon 14 from different angles. The collar 16 is the proximal side of the spoon 14 that is used to dock the handle 12. The hub 14 defines an annular aperture 35 that is open on its distal side to the space above the blade 18. The distal end of the blade 18 is contoured to form a tip 50 that is curved upwardly to help during the reduction and fixation of a fractured bone. As explained earlier, the blade 18 as shown is sized and shaped to be most useful during a scaphoid fracture surgery. The shape and size and curvature of the blade 18 may be specifically contoured depending on the bone that is fractured and in need of a reduction and fixation procedure.

EXAMPLE

FIGS. 10-22 are step-by-step drawings illustrating the use of the tool described herein in the example of a scaphoid fracture. FIGS. 1-9 illustrate a reduction and fixation tool as shown in the procedure drawings. In general, the tool will have a handle that is cannulated with a central bore for the guide wire and a parallel channel offset 2 mm, 4 mm, 6 mm or other offset distance from the central bore. The appropriate offset bore accommodates a second "corrected" guide wire if the first guide wire placed is not centered in the axis of the scaphoid. Alternatively, the parallel channel may be offset 4 mm, 6 mm or other distance from the central bore. There may also be various additional bores that enter the sides of the handle at 30, 50, 70, 10° and 12° (or other preferred angles) respectively and terminate in the central hole in the first face of the truncated, docking end of the handle. These alternative bores accommodate "corrected" guide wires if the first one placed is off-angle. Thus, the articular cartilage covering the proximal end of the scaphoid is not subjected unnecessarily to multiple, disruptive, guidewire holes seeking the central axis of the bone. In this scaphoid procedure example, the spoon is narrow, curved and tapered to be introduced through a small incision on the back of the wrist and advanced distally beneath the scaphoid, elevating the typically flexed distal fragment of the fractured scaphoid (or other bone). The spoon supports the reduced scaphoid fracture in place while the guide wire(s) are introduced through the handle, through the proximal fracture fragment, across the fracture site and into the distal fracture fragment.

Figure 10:
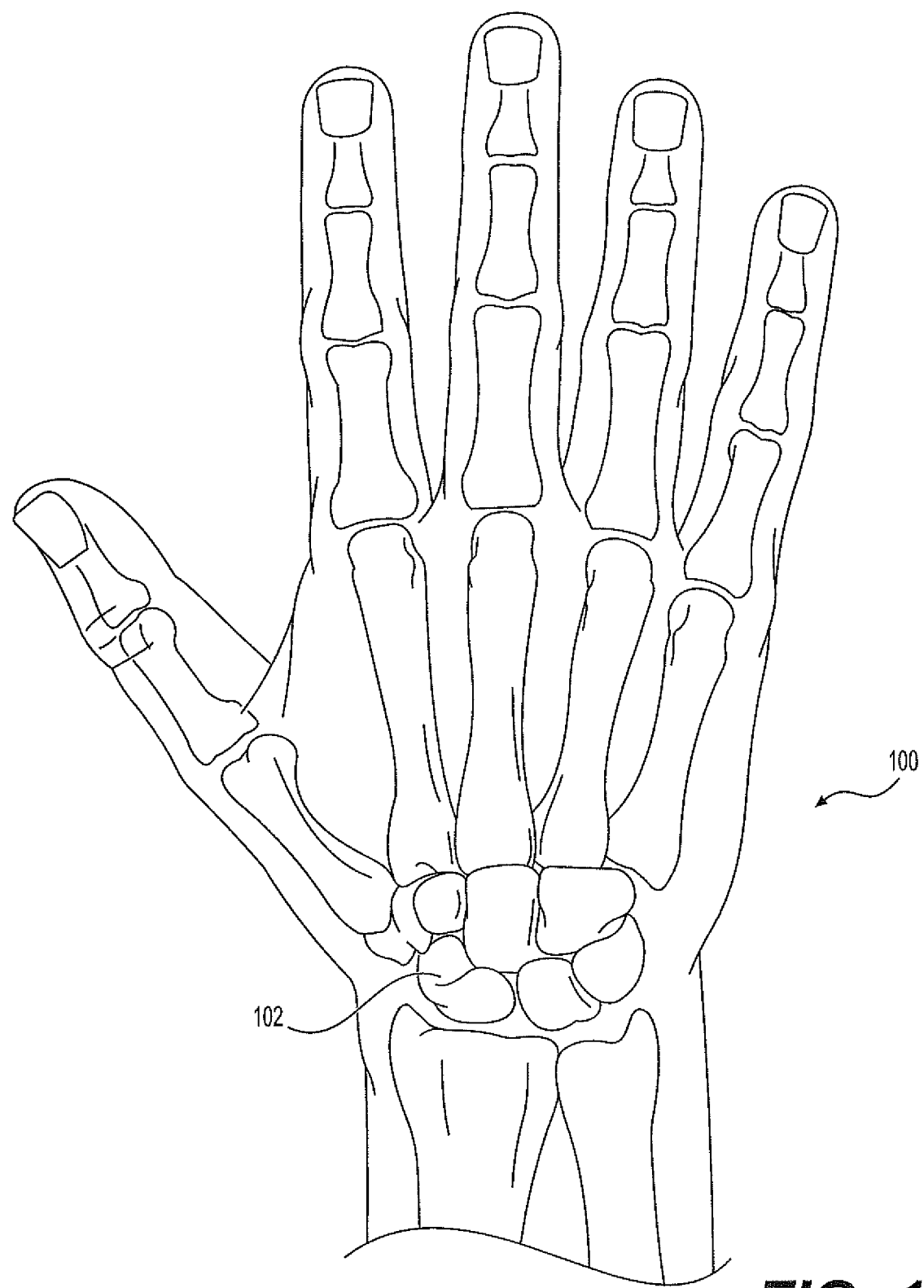
FIG. 10 is a top view of a healthy right hand illustrating the bone structure of the hand.

Turning again to the drawings, FIG. 10 is a top view of the back of right wrist 100 showing normal orientation of bones, including a normal, healthy scaphoid 102.

Figure 11:
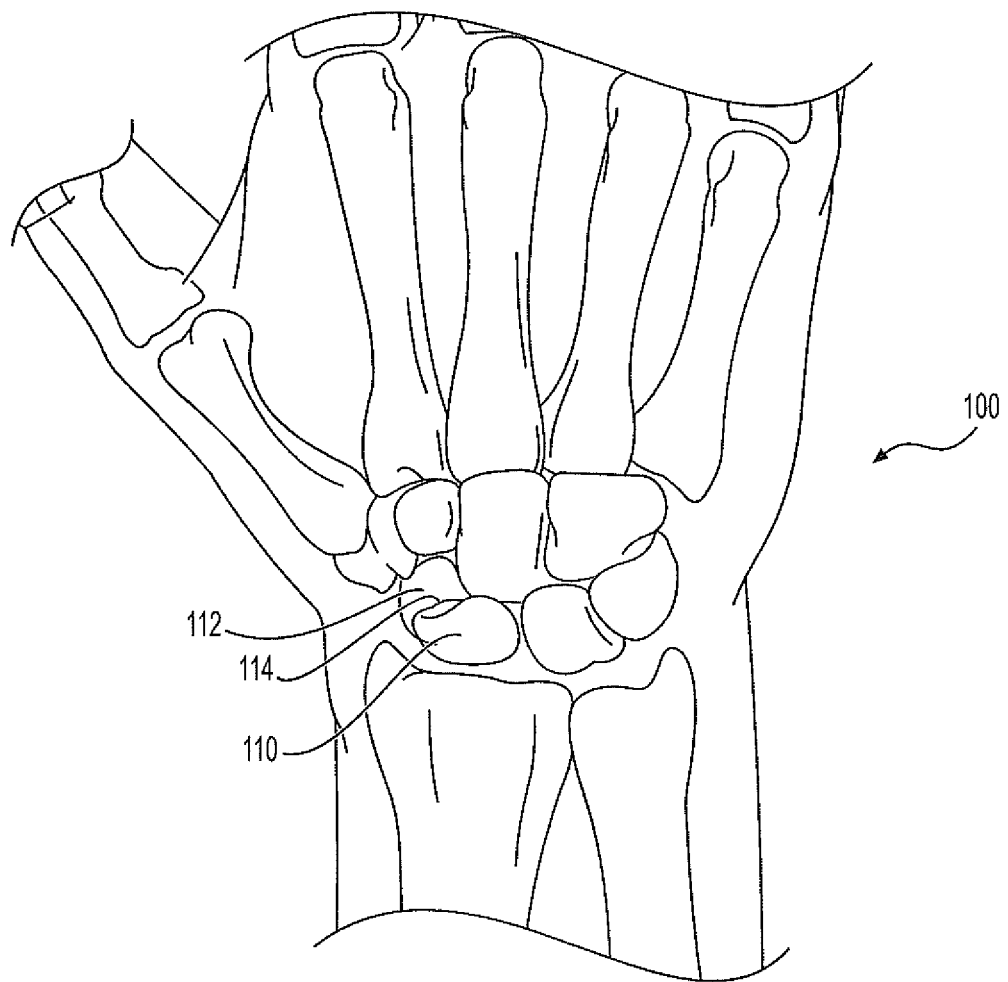
FIG. 11 is a top view of a right hand having a scaphoid fracture.
Figure 12:
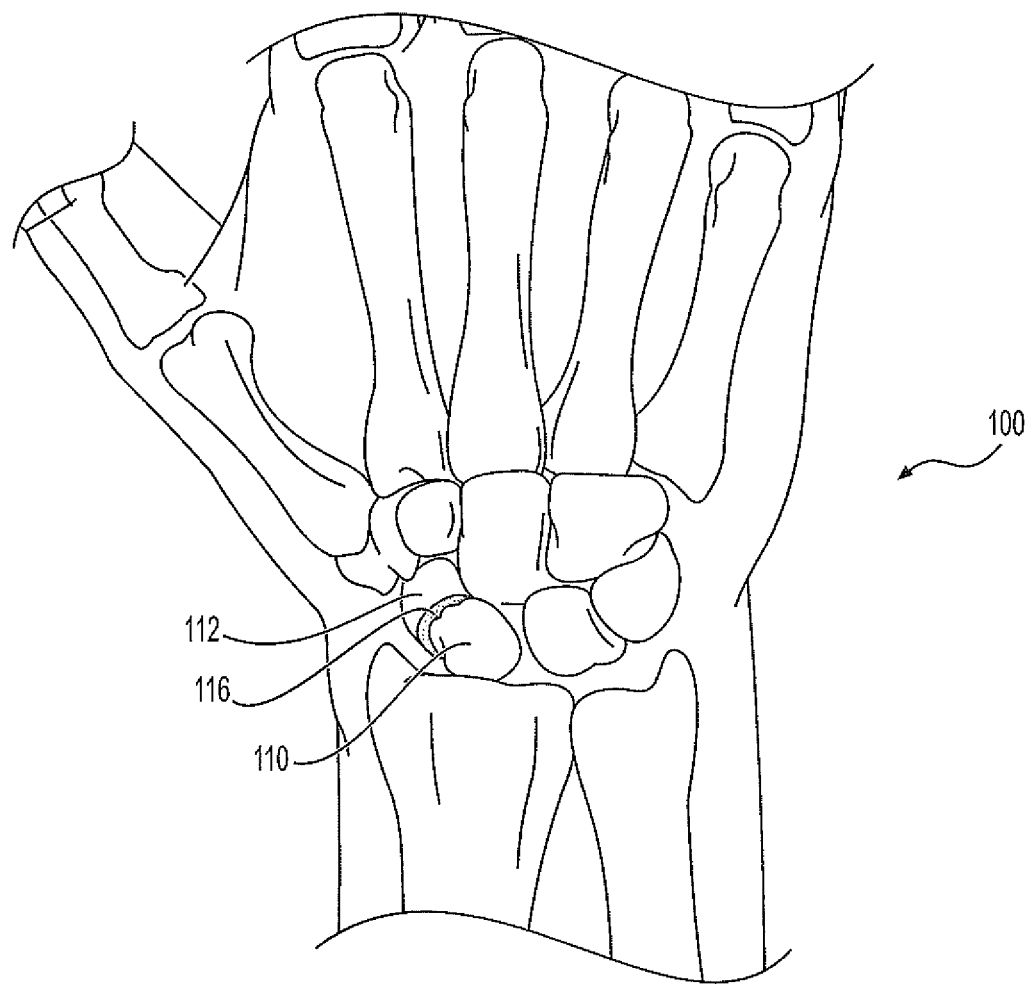
FIG. 12 is a top view of a right hand having a displaced scaphoid fracture.

FIG. 11 is a top view of the right wrist 100 showing a non-displaced fracture of the scaphoid wherein the scaphoid has a proximal fracture fragment 110 and a distal fracture fragment 112 and the fracture 114. FIG. 12 shows a displaced fracture of scaphoid, right wrist. In FIG. 12, the fracture 116 is shown to be displaced as compared with the fracture 114 in FIG. 11.

Figure 13:
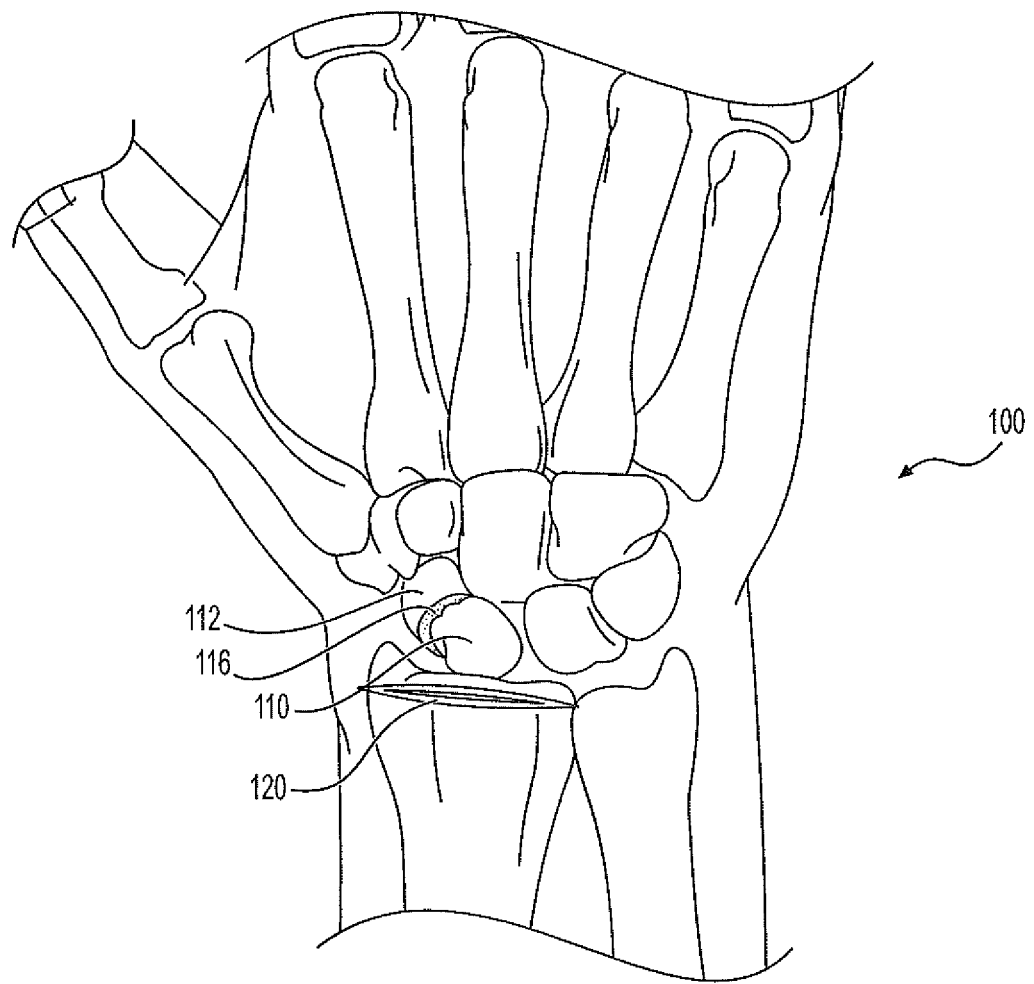
FIG. 13 is a top view of a hand with an incision as set forth in the method described herein.
Figure 14:
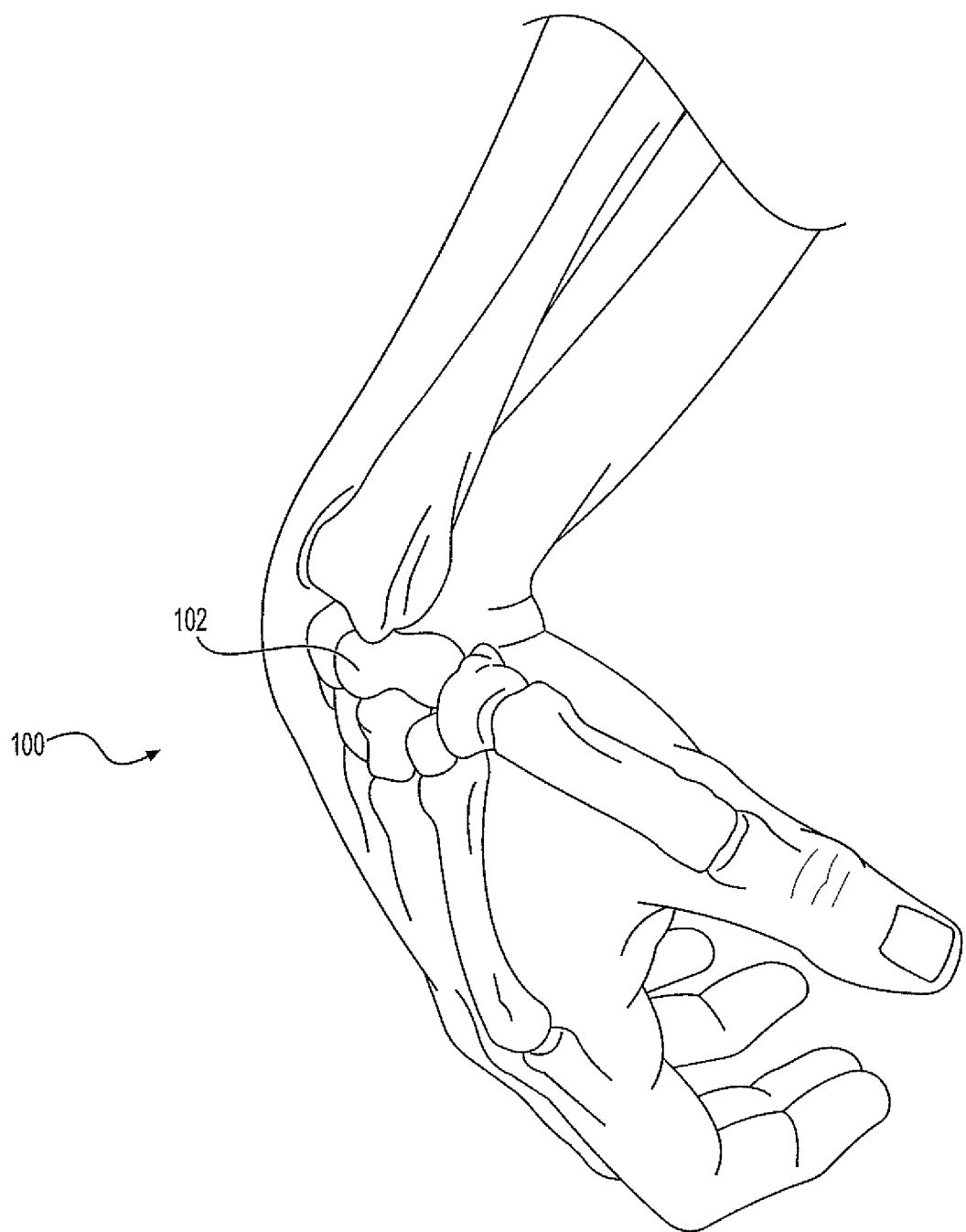
FIG. 14 is a side perspective view of a healthy right hand.

The reduction and fixation procedure begins in FIG. 13 with a transverse surgical incision 120 to approach the displaced fracture of the scaphoid from the back of the wrist. As illustrated in FIG. 14, flexion of the wrist 100 orients the scaphoid 102 in a near-horizontal position to present access to the central axis of the scaphoid from the proximal end of bone.

Figure 15:
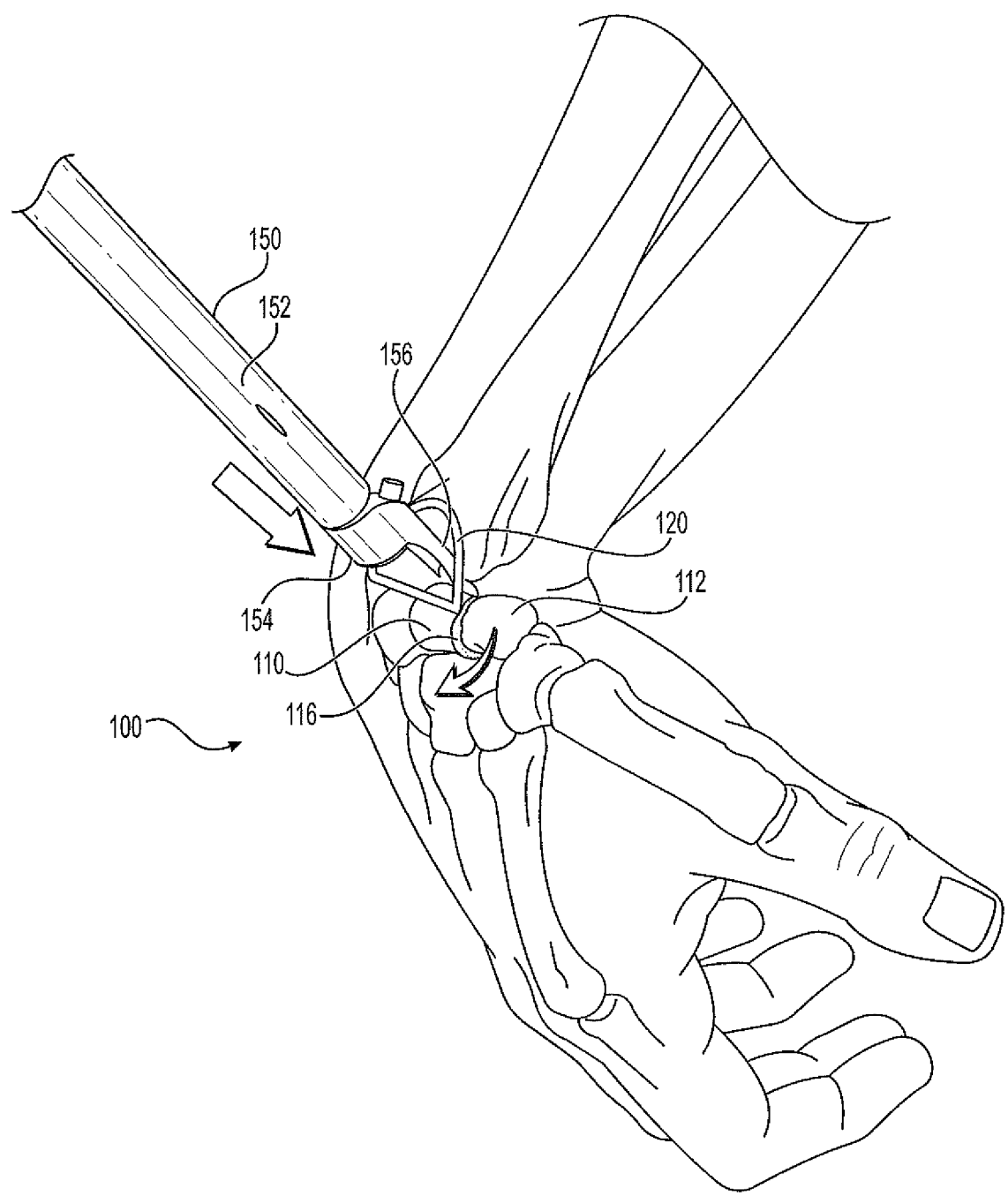
FIGS. 15 and 16 are a side perspective views of a right hand with a scaphoid fracture and a tool as described herein.
Figure 16:
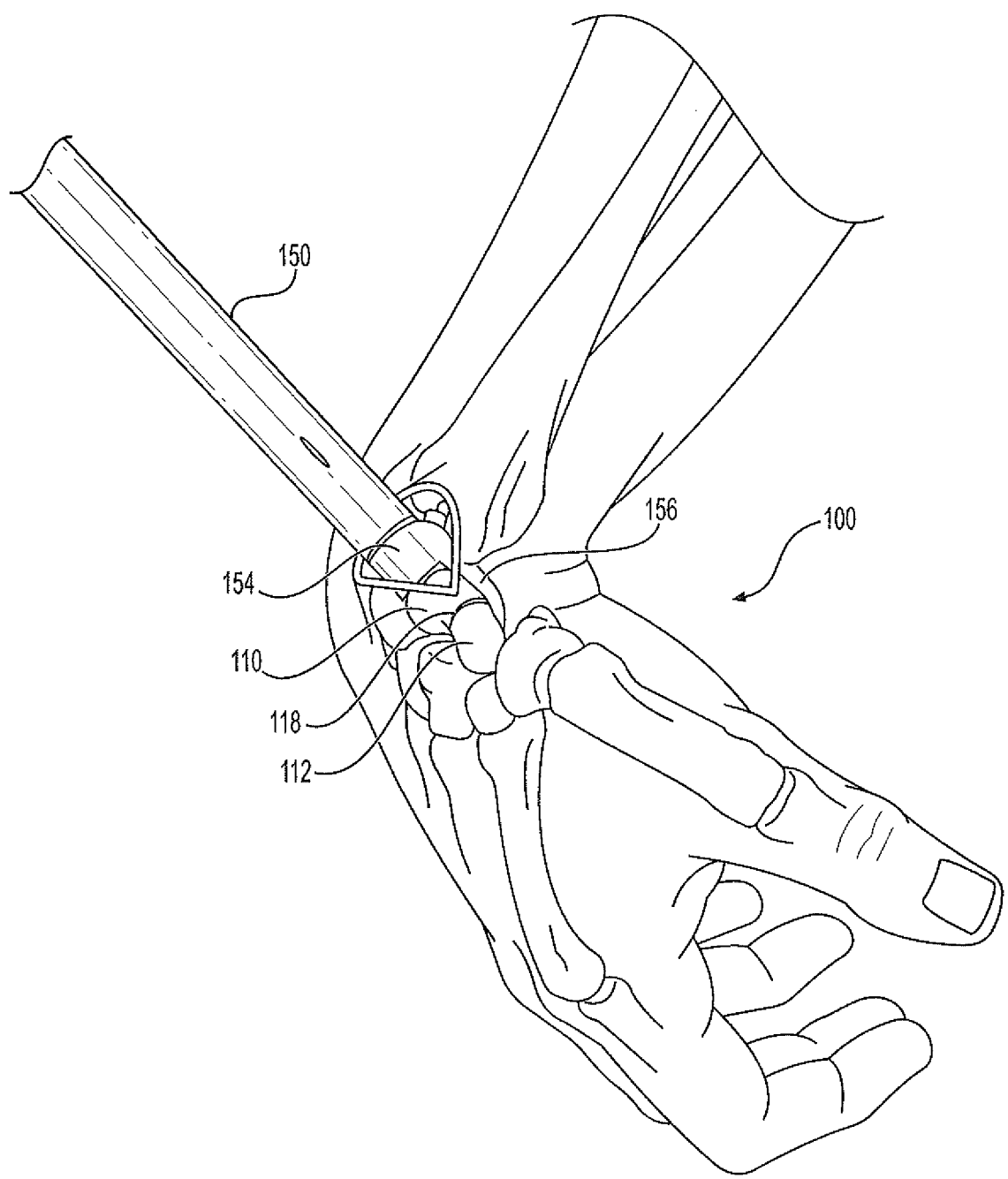

In FIG. 15, the reduction fixation tool 150, assembled with handle 152, is inserted beneath the fractured scaphoid 110 and 112 to enable the blade 156 to lift or leverage the flexed distal fragment 112 upward, thereby reducing the fracture 116. FIG. 16 shows the scaphoid fragments 110 and 112 reduced so that the reduced fracture 118 is in proper alignment.

Figure 17:
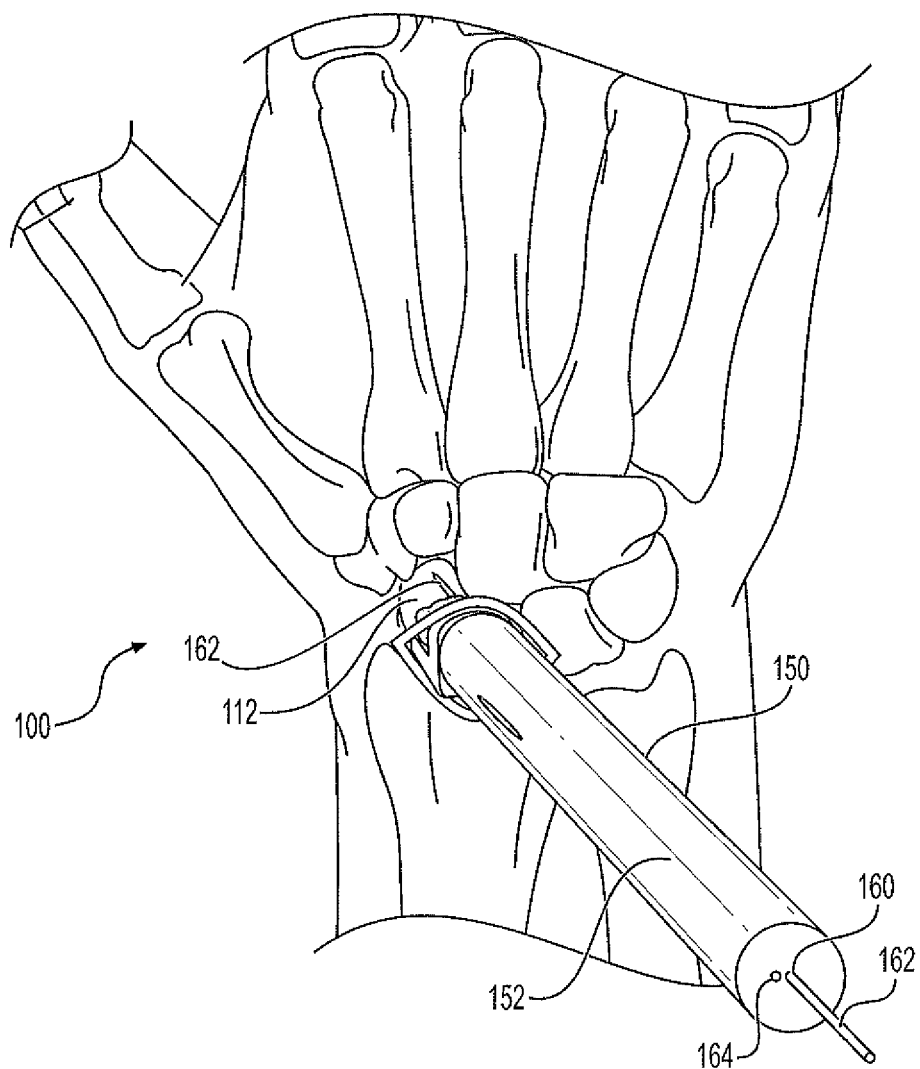
FIGS. 17 and 18 are top views of a hand with a fractured scaphoid and the tool in different procedural positions.
Figure 18:
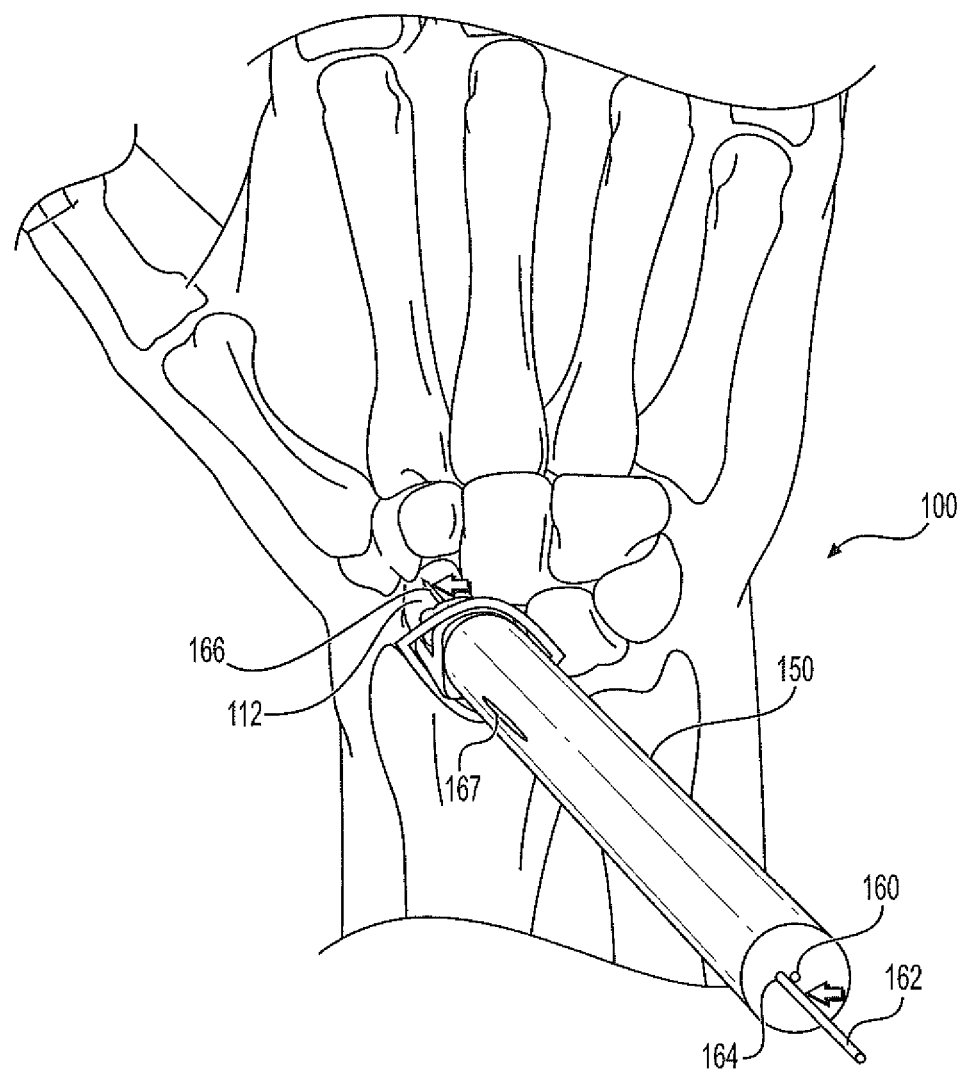

In FIG. 17, there is shown a surgeon's view of the proximal end of handle 152 for insertion of guide wire 162 through central bore 160. FIG. 18 illustrates the insertion of a second guide wire 166, offset 2 mm in any chosen direction through a second bore 164, if fluoroscopy shows the first wire 162 is not in the absolute central axis of the scaphoid.

Figure 19:
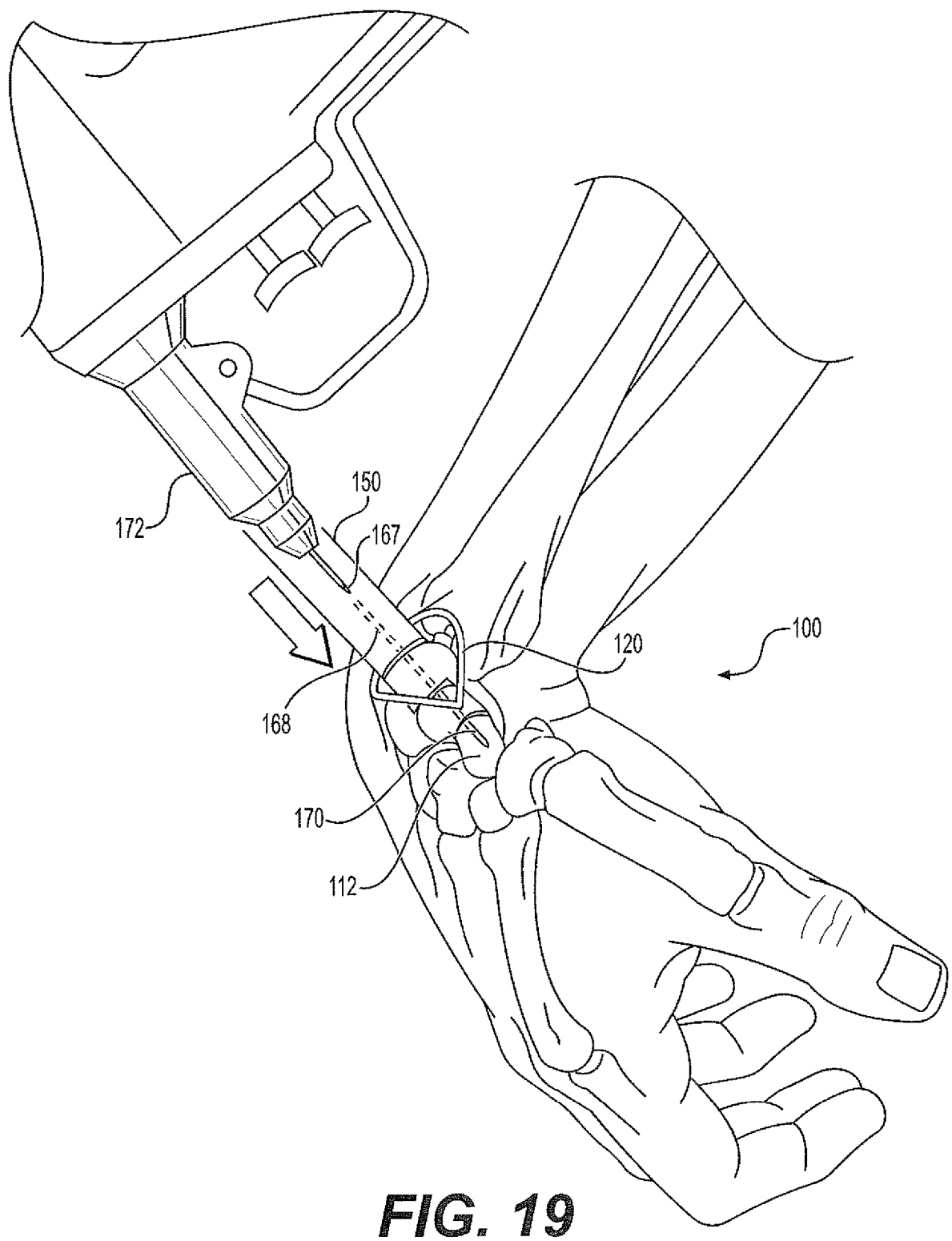
FIGS. 19 and 20 are side views of the hand and tool and a further device for setting a guide wire and a cannulated drill for use in the fixation procedure.

FIG. 19 illustrates a powered guide wire driver 172 inserting a second alternative guide wire 168 through the optional 10° angled bore 167 of the handle 150, if fluoroscopy shows the first guide wire is angled 10° from the central axis of scaphoid.

Figure 20:
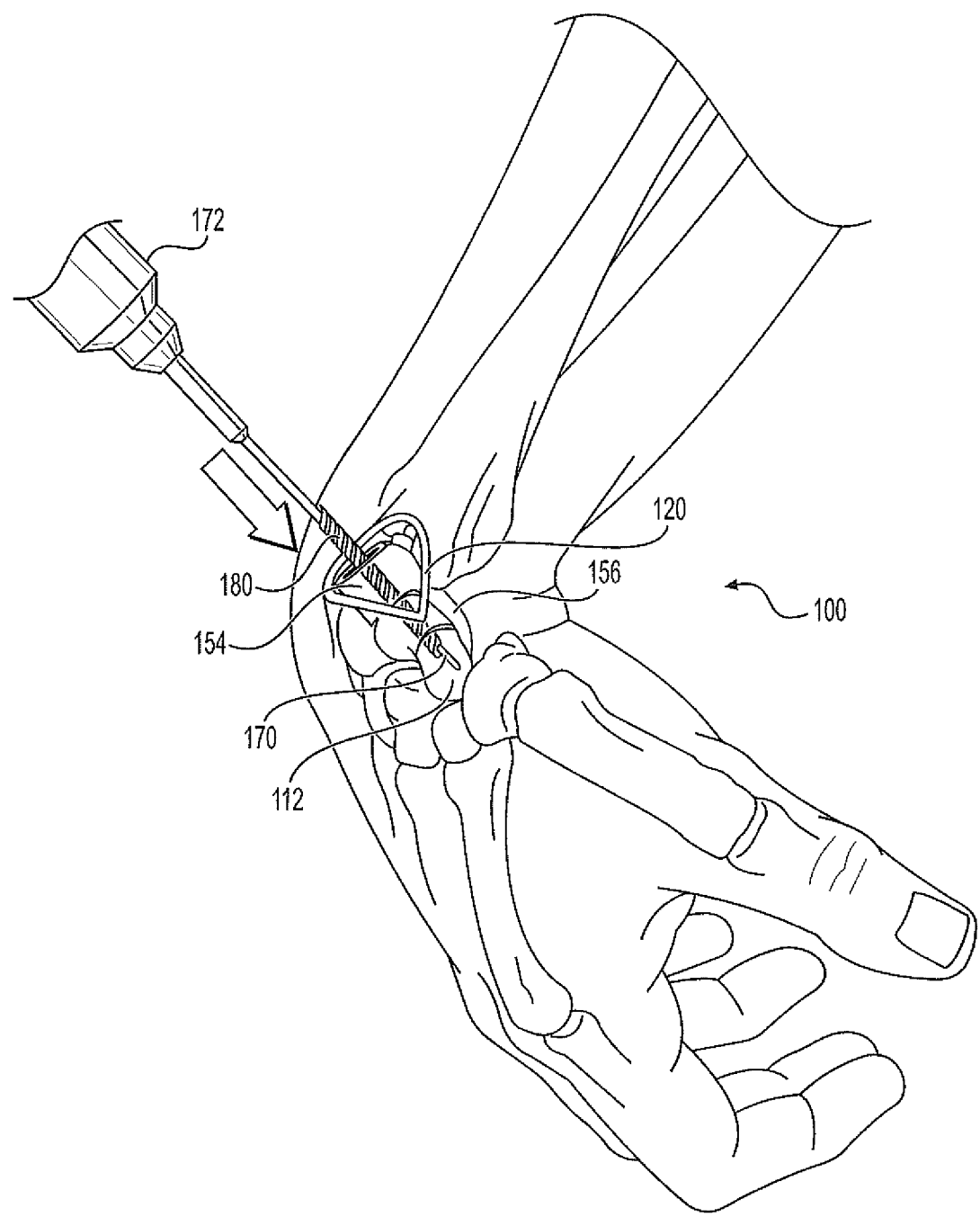
Figure 21:
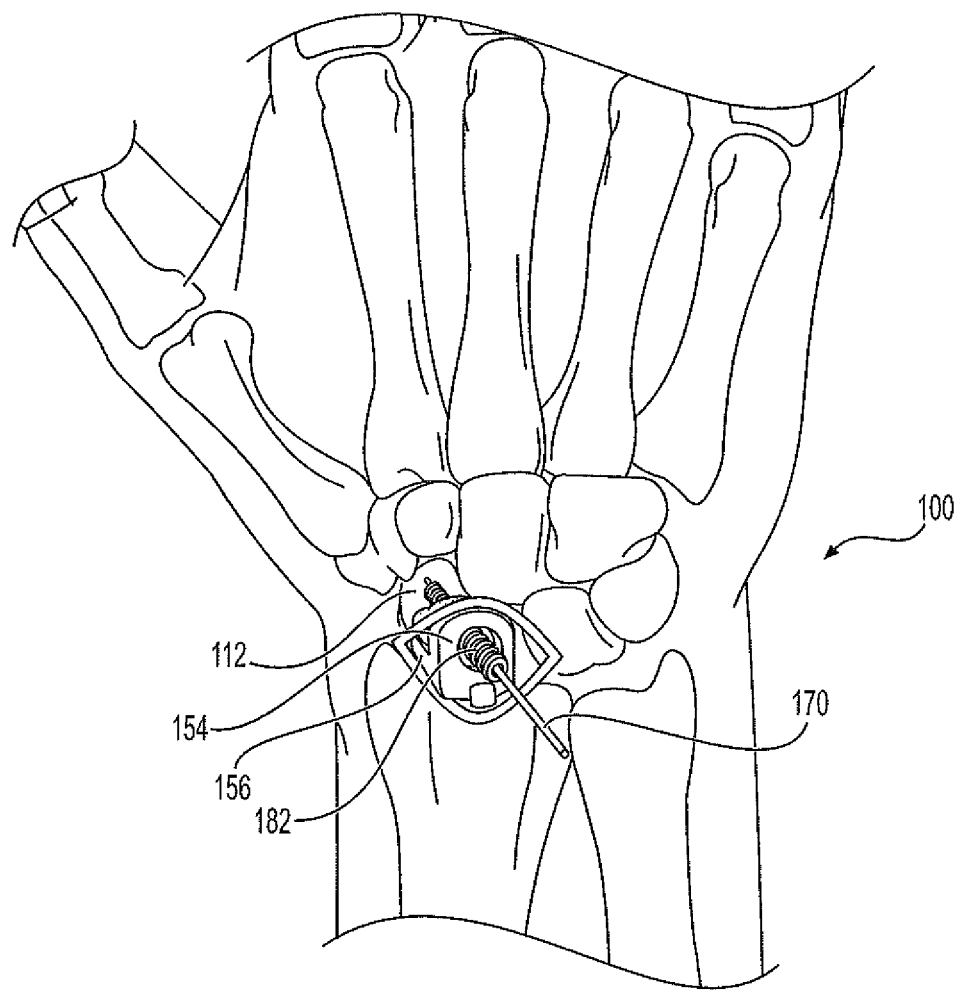
FIG. 21 is a top view of the hand with a cannulated screw being placed across a scaphoid fracture.
Figure 22:
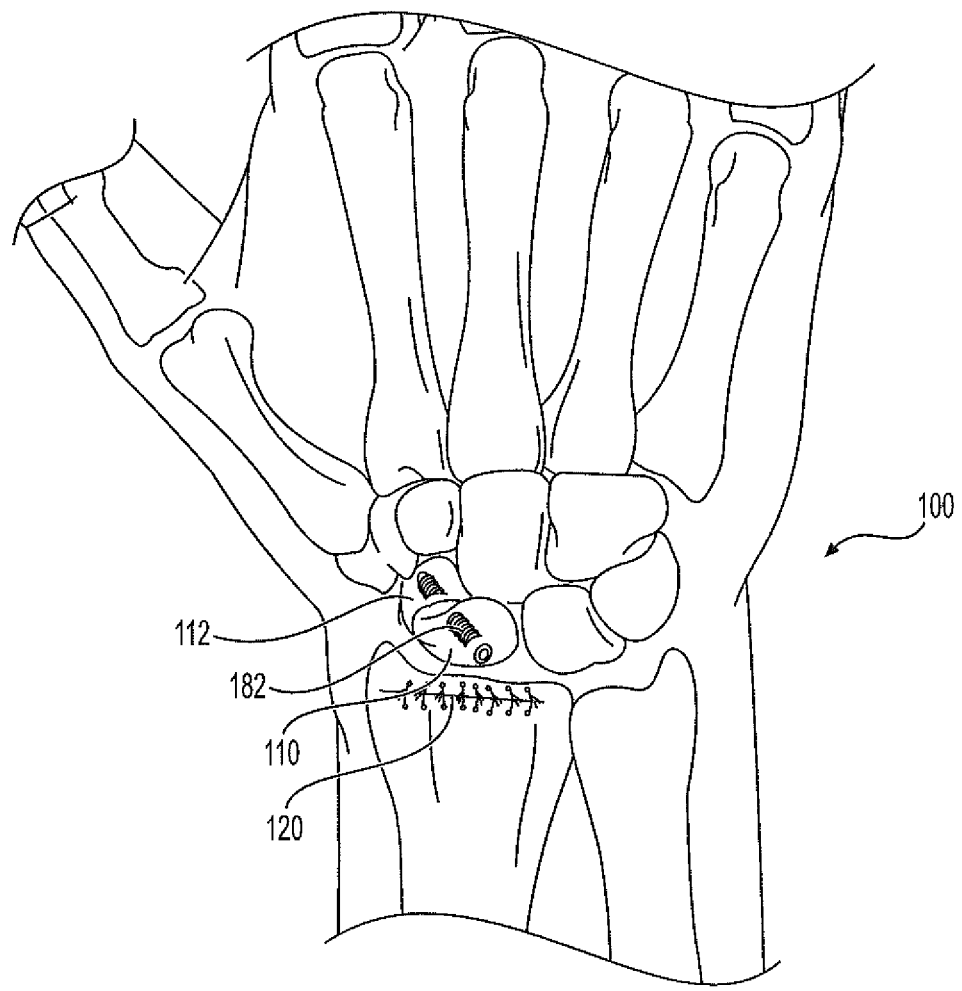
FIG. 22 is a top view of the repaired scaphoid fracture with a stitched incision.

In FIG. 20, the handle has been removed from the spoon to which it was docked by sliding it off the "corrected" guide wire 170, leaving the "corrected" central axial guide wire 170 in place to provisionally stabilize the reduced bone fracture fragments. A cannulated drill bit 180 prepares the hole for a fixation screw over the guide wire 170. FIG. 21 depicts a cannulated fixation/compression screw 182 inserted over the guide wire 170 to stabilize the scaphoid fracture. And finally, FIG. 22 shows the closed incision 120 after correct placement of a fixation screw 182 across the scaphoid fracture. The scaphoid fracture has been rigidly stabilized and the wrist can be placed in a cast or appropriate external splint for soft tissue healing.

Other embodiments of the present invention will be apparent to those skilled in the art from consideration of the specification. It is intended that the specification and figures be considered as exemplary only, with a true scope and spirit of the invention being indicated by the claims.

That which is claimed is:

1. A reduction and fixation tool for use in orthopaedic fracture repair, the tool comprising:
    a spoon and a handle,
    wherein the spoon is comprised of a proximal hub and a distal blade, wherein the distal blade is substantially flat and thin but has a contoured portion of a distal edge of the blade,
    wherein the handle has a length and has a first end and second end on opposite ends of the handle, wherein the handle has a first face on the first end and second face on the second end of the handle, and wherein the first end of the handle is positioned inside the proximal hub of the spoon,
    wherein the hub has a linear aperture therethrough that is open on a forward side above the blade portion of the spoon, and
    wherein the handle is cannulated and has a plurality of bores therethrough that are is open at the first face of the handle and at least two bores have and define the same opening at the first face.

2. A reduction and fixation tool for use in orthopaedic fracture repair as described in claim 1,
    wherein at least one of the bores is a longitudinal bore through the entire length of the handle and that is open at both the first face and second face of the handle.

3. A reduction and fixation tool for use in orthopaedic fracture repair as described in claim 2,
    wherein the at least one bore is generally positioned through the longitudinal center of the handle and is open at substantially the center of the first face.

4. A reduction and fixation tool for use in orthopaedic fracture repair as described in claim 1,
    wherein the plurality of bores are open at a plurality of different opening positions on the first face of the handle.

5. A reduction and fixation tool for use in orthopaedic fracture repair as described in claim 1,
    wherein the hub aperture is round and defines an inside diameter, wherein the handle first end is round in cross section and defines an outside diameter, and wherein the inside diameter of the hub aperture is slightly larger than the outside diameter of the first end of the handle to enable circular rotation of the handle in the hub.

6. A reduction and fixation tool for use in orthopaedic fracture repair as described in claim 5,
    wherein the first end of the handle has a frusto-conical shape in length that is positioned inside the hub aperture of the spoon.

7. A reduction and fixation tool for use in orthopaedic fracture repair as described in claim 1,
    wherein the contoured portion of the distal edge of the blade is a shape selected from the group consisting of a point, a barb, a fork, and a cup.

8. A method of reduction and fixation of a scaphoid bone fracture comprising the steps of:
    providing a reduction and fixation tool comprising a spoon and a handle,
    wherein the spoon is comprised of a proximal hub and a distal blade, wherein the distal blade is substantially flat and thin but has a contoured portion of a distal edge of the blade,
    wherein the handle has a length and has a first end and second end on opposite ends of the handle, wherein the handle has a first face on the first end and second face on the second end of the handle, and wherein the first end of the handle is positioned inside the proximal hub of the spoon,
    wherein the hub has a linear aperture therethrough that is open on a forward side above the blade portion of the spoon, and
    wherein the handle is cannulated and has a bore therethrough that is open at the first face of the handle;
    making an incision on the back of the wrist of a patient;
    positioning the spoon under the scaphoid bone of the patient;
    lifting a distal fragment of the patient's scaphoid bone into a desired anatomical alignment using the blade portion of the spoon that is external to the fragment and that externally contacts the distal fragment;
    positioning the handle bore opening on the first face of the handle adjacent to the scaphoid bone;
    inserting a guide wire through the bore and into the proximal scaphoid bone fragment and across the fracture and into the distal bone fragment;
    reaming the bone with a cannulated reamer over the guide wire to make a track for placement of a screw;
    then placing a cannulated screw over the guide wire and screwing the screw into the scaphoid bone and across the fracture to stabilize the fracture for healing.

9. A method of reduction and fixation of a scaphoid bone fracture as described in claim 8,
    further comprising the step of taking a scan of the scaphoid bone after the guide wire is inserted and before the screw is fixed into the bone in order to confirm the correct placement of the guide wire in the bone.

* * * * *